US008404449B2

(12) United States Patent
Bayley et al.

(10) Patent No.: US 8,404,449 B2
(45) Date of Patent: *Mar. 26, 2013

(54) STOCHASTIC SENSING THROUGH COVALENT INTERACTIONS

(75) Inventors: Hagan Bayley, College Station, TX (US); Seong-Ho Shin, College Station, TX (US); Tudor Luchian, College Station, TX (US); Stephen Cheley, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 700 days.

This patent is subject to a terminal disclaimer.

(21) Appl. No.: 12/429,897

(22) Filed: Apr. 24, 2009

(65) Prior Publication Data

US 2009/0283422 A1 Nov. 19, 2009

Related U.S. Application Data

(63) Continuation of application No. 10/434,897, filed on May 9, 2003, now abandoned.

(60) Provisional application No. 60/379,527, filed on May 10, 2002, provisional application No. 60/450,930, filed on Feb. 28, 2003.

(51) Int. Cl.
*G01N 33/53* (2006.01)
(52) U.S. Cl. ...................................... 435/7.1
(58) Field of Classification Search ............... None
See application file for complete search history.

(56) References Cited

U.S. PATENT DOCUMENTS

| | | | | |
|---|---|---|---|---|
| 2,165,892 | A | 7/1939 | Green et al. | 177/351 |
| 2,592,737 | A | 10/1950 | Reynolds et al. | 177/351 |
| 4,661,235 | A | 4/1987 | Krull et al. | 204/414 |
| 4,824,529 | A | 4/1989 | Thompson et al. | 204/1 T |
| 5,204,239 | A | 4/1993 | Gitler et al. | 435/7.1 |
| 5,234,566 | A | 8/1993 | Osman et al. | 204/403 |
| 5,368,712 | A | 11/1994 | Tomich et al. | 204/403 |
| 5,436,170 | A | 7/1995 | Cornell et al. | 436/527 |
| 5,443,955 | A | 8/1995 | Cornell et al. | 435/7.21 |
| 5,637,201 | A | 6/1997 | Raguse et al. | 204/418 |
| 5,693,477 | A | 12/1997 | Cornell et al. | 435/7.1 |
| 5,736,342 | A | 4/1998 | Van Wie et al. | 435/7.2 |
| 5,741,712 | A | 4/1998 | Cornell et al. | 436/501 |
| 5,753,093 | A | 5/1998 | Raguse et al. | 204/418 |
| 5,766,960 | A | 6/1998 | Cornell et al. | 436/501 |
| 5,777,078 | A | 7/1998 | Bayley et al. | 530/350 |
| 5,798,030 | A | 8/1998 | Raguse et al. | 204/403 |
| 5,874,316 | A | 2/1999 | Cornell et al. | 436/518 |
| 6,030,782 | A | 2/2000 | Anderson et al. | 435/6 |
| 6,127,166 | A | 10/2000 | Bayley et al. | 435/252.3 |
| 6,177,000 | B1 | 1/2001 | Peterson | 205/777.5 |
| 6,224,885 | B1 | 5/2001 | Jenner et al. | 424/401 |
| 6,267,872 | B1 | 7/2001 | Akeson et al. | 205/775 |
| 6,375,962 | B2 | 4/2002 | Jenner et al. | 424/401 |
| 6,426,231 | B1 | 7/2002 | Bayley et al. | 436/518 |
| 6,498,043 | B1 | 12/2002 | Schulman et al. | 438/1 |
| 6,641,997 | B1 | 11/2003 | MacKinnon | 435/6 |
| 6,664,280 | B2 | 12/2003 | Lin et al. | 514/358 |
| 6,824,659 | B2 * | 11/2004 | Bayley et al. | 204/403.01 |
| 6,842,659 | B2 | 1/2005 | Parikh et al. | 700/121 |
| 6,846,947 | B2 | 1/2005 | Farone et al. | 560/147 |
| 6,916,665 | B2 * | 7/2005 | Bayley et al. | 436/149 |
| 6,927,070 | B1 | 8/2005 | Bayley et al. | 436/518 |
| 7,179,587 | B2 | 2/2007 | van der Weide | 435/4 |
| 7,429,316 | B1 * | 9/2008 | Osipchuk | 204/403.01 |
| 7,867,716 | B2 * | 1/2011 | Kang et al. | 435/7.1 |
| 2002/0094526 | A1 | 7/2002 | Bayley et al. | 435/6 |
| 2004/0022701 | A1 | 2/2004 | Segal et al. | 422/186.04 |
| 2004/0191845 | A1 | 9/2004 | Bayley et al. | 435/7.33 |
| 2005/0014129 | A1 | 1/2005 | Cliffel et al. | 435/4 |
| 2005/0131211 | A1 | 6/2005 | Bayley et al. | 530/350 |
| 2005/0208574 | A1 | 9/2005 | Bayley et al. | 435/6 |

FOREIGN PATENT DOCUMENTS

| | | | |
|---|---|---|---|
| EP | 0 441 120 | 1/1991 | |
| WO | 96/12957 | 5/1996 | |
| WO | 97/20203 | 6/1997 | |
| WO | WO 01/59453 | * | 8/2001 |

OTHER PUBLICATIONS

Liu ["Dynamic Rearrangement of the Outer Mouth of a K+ Channel during Gating" Neuron, vol. 16, 859-867].*
Movileanu ["Location of a Constriction in the Lumne of a Transmembrane Pore by Targeted Covalent Attachment of Polymer Molecules" J. Gen. Physiol., vol. 117, Mar. 2001, 239-251].*
Tien, H.T. et al.; "Electrochemistry of support bilayer lipid membranes: background and techniques for biosensor development"; Bioelectrochem. Bioenergetics; 1997, 42: 77-94.
Rosen, B.P.; "Families of arsenic transporters"; Trends Microbiol. 1999; 7: 207-212.
Klein, I. et al.; "An inventory of the human ABC proteins"; Biochim. Biophys. ACTA. 1999; 1461:237-262.
Griffin, B.A.; "Specific Covalent Labeling of Recombinant in Living Cells"; dissertation, Univ. Calif. San Diego (1998) (141-142, pages).
Griffin, B.A., et al.; "Fluorescent labeling of recombinant proteins in living cells with FlAsH"; Methods Enzymol. 2000;327:565-578.
Siegel, M.S., et al.; "A genetically encoded optical probe of membrane voltage"; Neuron. 1997;19:735-741.

(Continued)

*Primary Examiner* — Ann Lam
(74) *Attorney, Agent, or Firm* — Baker Botts L.L.P.

(57) ABSTRACT

A system and method for stochastic sensing in which the analyte covalently bonds to the sensor element or an adaptor element. If such bonding is irreversible, the bond may be broken by a chemical reagent. The sensor element may be a protein, such as the engineered $P_{SH}$ type or αHL protein pore. The analyte may be any reactive analyte, including chemical weapons, environmental toxins and pharmaceuticals. The analyte covalently bonds to the sensor element to produce a detectable signal. Possible signals include change in electrical current, change in force, and change in fluorescence. Detection of the signal allows identification of the analyte and determination of its concentration in a sample solution. Multiple analytes present in the same solution may be detected.

20 Claims, 6 Drawing Sheets

OTHER PUBLICATIONS

Liu, Y., et al.; "Dynamic rearrangement of the outer mouth of a K+ channel during gating"; Neuron. 1996;16:859-867.

Fidder, A., et al.; "Biomonitoring of exposure to lweisite based on adducts to hemoglobin"; Arch. Toxicol. 2000;74:207-214.

International Search Report with Notification of Transmittal of Search Report, PCT/US03/14797; 10 pages, Mailed Sep. 11, 2003.

Bayley, Hagan, et al., "Stochastic sensors inspired by biology", Nature (London), vol. 413, No. 6852; pp. 226-230, XP-002252374, Sep. 13, 2001.

Gu, Li-Qun, et al., "Stochastic sensing of organic analytes by a pore-forming protein containing a molecular adapter", Nature (London), pp. 686-690, XP-002252375, Apr. 22, 1999.

Hodneland, Christian, et al., "Selective immobilization of proteins to self-assembled monolayers presenting active site-directed capture ligands", Proceedings of the National Academy of Sciences of the United States, vol. 99, No. 8, pp. 5048-5052, XP-002252376, Apr. 16, 2002.

Movileanu, Liviu, et al., "Detecting protein analytes that modulate transmembrane movement of a polymer chain within a single protein pore", Nature Biotechnology, vol. 18, pp. 1091-1095, XP-002188230, Oct. 2000.

PCT Written Opinion for US03/14797, 5 pages, Mailed Jul. 22, 2004.

Braha et al., "Simultaneous Stochastic Sensing of Divalent Metal Ions", Nature biotechnology, vol. 18, pp. 1005-1007, Sep. 2000.

Movileanu et al., "Location of a Constriction in the Lumen of a Transmembrane Pore by Targeted Covalent Attachment of Polymer Molecules", The Rockefeller University Press, vol. 17, pp. 239-251, Mar. 2001.

"Location of a Constriction in the Lumen of a Transmembrane Pore by Targeted Covalent Attachment of Polymer Molecules" by Liviu Movileanu, Stephen Cheley, Stefan Howorka, Orit Braha, & Hagan Bayley; *J. Gen Phyisol*, vol. 117, pp. 239-251, Mar. 1, 2001.

European Office Action; Application No. 03 738 910.3-2404; pp. 6, Mar. 12, 2012.

* cited by examiner

STOCHASTIC SENSING THROUGH COVALENT INTERACTIONS

PRIORITY CLAIM

The present invention claims priority under 35 U.S.C. §120 as a continuation application of U.S. patent application Ser. No. 10/434,897, filed May 9, 2003, now abandoned which claims priority under 35 U.S.C. §119(e) to U.S. Provisional Patent Application Ser. No. 60/379,527, filed May 10, 2002, and U.S. Provisional Patent Application Ser. No. 60/450,930, filed Feb. 28, 2003.

STATEMENT OF GOVERNMENT FUNDING

The present invention was developed using funding from the U.S. Department of Energy, a Department of Defense (Office of Naval Research) Multidisciplinary Research Initiative (1999), and the National Institutes of Health. The U.S. government may have certain right to the invention.

FIELD OF THE INVENTION

The invention relates to new methods and systems for stochastic sensing in which the analyte becomes transiently or permanently attached to the sensor element through covalent bonding. The invention also relates to the use of chemical reagents to reverse such covalent bonding.

BACKGROUND

Stochastic sensing is based on the detection of individual binding events between analyte molecules and a single sensor element. Upon binding, a property of the sensor element is altered. This property or the effects of the changed property are measured.

In a simple example, the sensor element is a protein that is altered when it binds another molecule. The binding molecule to be detected is referred to as the analyte. The alteration of the sensor element that occurs upon binding is measured either directly or indirectly. In simple systems the alteration produces a simple signal, such as a difference in electrical current, force or fluorescence. Measurements of the signal indicate whether the analyte is bound and how long it remains bound. The frequency of occurrence of binding events is determined by the concentration of the analyte. The nature of the binding event is determined by the binding properties of the analyte, which determine, for example, the magnitude and duration of the resulting signal. Thus, a single sensor element to which multiple analytes may bind either directly may be used to determine which of those analytes are in a solution and the concentration of each particular analyte.

Although in simpler systems the sensor element has one binding site to which all analytes bind directly, it is possible for the sensor to have multiple binding sites, with different sites for different analytes. Additionally, a host or adaptor molecule may be used to facilitate binding of the analyte to the sensor element. The host molecule may merely facilitate the direct interaction of the analyte and sensor element, or it may serve as an adaptor that binds to both the analyte and the sensor element and allows connection of the two.

Stochastic sensing may be accomplished with various sensing elements, using various modes of detection. One simple model uses an ion channel protein pore embedded in a membrane between a cis chamber and a trans chamber. When the pore is fully open a large ion flux occurs (e.g. $10^8$ ions/s) which constitutes an electrical current that may be monitored by single channel recording. When an analyte binds to the pore, ion flux is altered, usually by decreasing the flow of ions. This generates a current trace which shows conduction over time.

Figure 1:
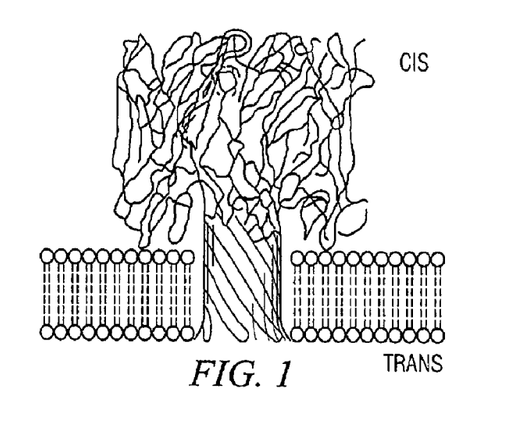
FIG. 1 illustrates a molecular graphics rendition of the $P_{SH}$ version of the αHL heptamer pore as used in certain embodiments of the present invention. In $P_{SH}$, one of the seven αHL subunits has been replaced with a mutated subunit containing a Cys residue in place of the naturally occurring Thr-117.

One particular pore that has been used in stochastic sensing is Staph alpha hemolysin ($\alpha$(HL), which is actually an exotoxin secreted by *Staphylococcus aureus*. The monomeric 293 amino acid polypeptide can self-assemble on lipid bilayers, such as membranes, to form a heptameric pore. Alternatively, pre-formed pores may be inserted into a lipid bilayer. The pore is a mushroom-shaped structure in which the lower half of the stem forms a transmembrane channel. The interior of the pore is referred to as the "lumen" and may be accessible from outside the pore. By convention, when the pore is situated in a membrane, the side of the membrane on which the top of the mushroom shape is located is designated as the "cis" side of the membrane. The side of the membrane to which the stem portion leads is designated the "trans" side of the membrane. The pore essentially forms a hole in the membrane through which ions will flow if an electric potential is generated between the two chambers. (See FIG. 1.)

Stochastic sensing methods have been previously described in a number of publications, including U.S. Pat. No. 6,426,231 to Bayley et al. and a divisional application of that patent, U.S. patent application Ser. No. 10/180,792, filed Jun. 25, 2002. Protein pores for use in stochastic sensing and methods of using such pores have also been described in U.S. patent application Ser. No. 09/781,697 filed Feb. 12, 2001.

However, these previous manifestations of stochastic sensing have utilized non-covalent interactions between the analyte and the sensor element. There is considerable interest in the detection of reactive molecules including chemical warfare agents, pesticides, chemotherapeutic agents, and so on which will covalently bond to a sensor element. The reactivity of such molecules may be utilized to facilitate sensing and distinguish the reactive molecules from unreactive molecules.

SUMMARY OF THE INVENTION

The present invention relates to methodologies for stochastic sensing in which the analyte covalently bonds to a sensor element. Stochastic sensing through such covalent interactions permits the detection of reactive analytes by making use of their reactivity.

Such covalent interactions may be reversible or irreversible. Where the covalent reaction is reversible, individual reaction events are be resolved by the sensing system within reasonable time frame, and the distribution in time and the character of these reaction events may be used to detect both the concentration and identity of the analytes. Similarly, where the reaction is normally irreversible, but is reversed due to the present of a chemical reagent, both the concentration and identity of the analytes may be readily detected. Where the covalent reaction is irreversible and the analyte remains covalently bound to the sensor element, the character of a the signal produced by binding and its response to physical and chemical manipulations may reveal the identity of a single analyte molecule.

Using the methodologies of the present invention, the concentrations and identities of multiple analytes may be determined simultaneously. Furthermore, these determinations may even be observed on a millisecond time scale. Although these abilities were previously observed using analytes that do not covalently bond with sensor elements, the present invention allows the stochastic sensing of analytes that do covalently bond with the sensor element. Certain embodiments even allow detection of concentration of analytes that irreversibly bond with the sensor element by providing a chemical reagent that reverses the other otherwise irreversible bonding. Furthermore, because the present invention allows covalent bonding of the analyte, it allows distinction between reactive and unreactive analytes.

The following abbreviations are used throughout the specification and claims:

αHL—alpha hemolysin, a heptameric pore protein
BAL—British anti-Lewisite, 2,3-dimercaptopropanol
βME—2-mercaptoethanol
Cys—Cysteine, an amino acid
DTNB—5,5'-dithiobis(2-nitrobenzoic acid)
DTT—dithiothreitol
EDTA—ethylenediamine tetra-acetic acid, a metal chelating agent.

"Irreversible"—As used in the present application, "irreversible" designates a reaction which, under the specified conditions, has an extremely low dissociation rate or forms very stable covalent bond. In specific embodiments of the invention, an irreversible bond or reaction forms an association between at least two molecules that is too long-lived for stochastic sensing using that system or method, absent the presence of a specific chemical reagent that directly or indirectly causes dissociation or breaks the covalent bond.

KCl—Potassium chloride, a salt which dissociates to form $K^+$ and $Cl^-$ ions in water. These ions may be moved through an open pore in an electrical potential.

$P_{SH}$—(T117C-D8)$_1$(RL2)$_6$, an engineered αHL pore formed from six wild-type-like monomers and one mutated monomer in which Thr-117 is replaced with Cys, providing a sulfhydryl group within the lumen of the pore.

MOPS—a buffer used to maintain constant pH.
MTSES—(2-sulfonatoethyl)methane thiosulfonate to maintain constant pH.
MES—a buffer used in various solutions.
Thr—Threonine, an amino acid.
Tris—a buffer used to maintain constant pH In certain exemplary embodiments of the present invention, a system for sensing at least one reactive analyte in a sample is provided. The system includes a sensor element and a sample containing at least one reactive analyte. The reactive analyte covalently bonds to the sensor element. This covalent bond between the analyte and the sensor element may be a direct covalent bond between the analyte and the sensor element or it may be a covalent bond between the analyte and an adaptor molecule that then interacts with the sensor element, for instance through a covalent or non-covalent bond. Other host molecules that facilitate covalent bonding of the analyte to the sensor element may also be present.

The system may be used for stochastic sensing, where the sensor element produces a detectable signal when covalently bound to the reactive analyte. The sensor element may be a protein, including engineered proteins such as a protein pore. Because of the covalent bonding aspect of the system, it is capable of detecting reactive analytes among similar unreactive molecules. More than one sensor element may be used in a sensing system. Examples of reactive analytes that may be detected with the system include chemical weapons, environmental toxins, pharmaceuticals and food contaminants.

Signals produced upon analyte bonding include changes in electrical current, changes in force, and changes in fluorescence. In many embodiments with protein pore sensors the signal may be a change in the magnitude of an electrical current. In some embodiments of the invention, the signal may simply register a change in the condition. In other embodiments the nature of the change may be recorded and used in greater detail.

In some embodiments the reactive analyte may irreversibly covalently bond to the sensor element. In these systems, the sensor may simply detect bonding alone. It may also detect other properties of the analyte while it is bound to the sensor. For example, other chemicals may be added after initial detection of the analyte which produce additional signals to further identify or characterize the analyte. Additionally, in some embodiments of the invention the system may also include a chemical reagent capable of breaking the irreversible covalent bond between the analyte and the sensor element. This may allow detection of, for instance, concentration of the analyte, which may not be detectable if the irreversible covalent bond is not broken.

These systems may also be used to detect multiple analytes that may bond to the sensor element. In certain embodiments the sample tested contains at least a second reactive analyte that forms a covalent bond with the sensor element. As with the single analyte example, this may be a direct covalent bond or a covalent bond to an adaptor molecule. Different adaptor molecules, if present, may be provided for different analytes, or the system may be able to detect some analytes that require an adaptor and other that do not. Similarly, multiple analytes need not all bind to the same binding site of the sensor element.

Multiple analytes may be distinguished by differences in the signal produced when different analytes bond to the sensor element.

In more specific embodiments, a sensing devices is provided that contains a cis and a trans chamber connected by a protein pore. A detection system is set up so as to detect current between the chambers. If a potential is applied between the chambers while an ionic solution such as KCl is in them, the ions will move through the open protein pore, resulting in a detectable current. Bonding of a reactive analyte to the protein pore produces a change in the current. This is generally effected by causing a restriction of the pore. In many examples, the reactive analyte actually bonds within the lumen of the pore. Although the analyte may generally be on either side of the pore, the rate of covalent bond formation may be influenced by whether it is placed in the cis or trans chamber because the lumen may be more accessible from one side or the other. Generally the analyte is proved in only one chamber, although in certain embodiments of the invention it may be placed in both chambers.

The pore in these embodiments may be an αHL pore, particularly. Pores may be engineered proteins such as an αHL pore with at least one monomer having a Cys residue at amino acid 117. Such an engineered pore may be used to detect arsenicals.

If the analyte is such a system irreversibly bonds to the protein pore, a chemical reagent may be used to break the irreversible covalent bond. The chemical reagent is generally provided in one chamber, while the analyte is in the other chamber. However, other configurations in which the reagent and analyte may be together in one or both chambers are possible.

Current detection systems as described above may be used to detect and identify analytes. Different analytes tend to remain in the lumen for a different period of time. Thus the duration of any current change may be used to identify the analyte. The frequency of any current change caused by a specific analyte may be used to determine its concentration in the sample. A compilation of such current change signatures may be produced and used to quickly identify specific analytes within a sample containing multiple analytes.

The invention also includes methods for producing and using systems as described above. In certain methods the analyte is supplied in a sample to the sensor element, which remains in contact with the element for a given time period. In a sensor designed to be used multiple times, the sample may be removed and replaced with another sample after testing of the first sample is completed. Additionally, in some embodiments a constant sample stream may be provided to the sensor element.

In another embodiment, the invention relates to a system for sensing at least one reactive analyte in a solution. The system may include a sensing device separated into a trans chamber and a cis chamber by a divider. It also may include a protein pore operably disposed in the divider. It further may include a detection system operable to detect current between the cis and trans chambers. Finally, it may also include an ionic solution containing at least one reactive analyte capable of covalently bonding to the protein pore. Bonding of the reactive analyte to the protein pore produces a change in current between the cis and trans chambers detectable by the current detection system.

For a better understanding of the invention and its advantages, reference may be had to the following drawings and description of exemplary embodiments.

BRIEF DESCRIPTION OF THE DRAWINGS

FIG. 2 illustrates the interaction of 4-sulfophenylarsine oxide with the $P_{SH}$ pore, according to certain embodiments of the present invention. To obtain the data presented, single channel current traces were carried out for 1 second at −50 mV with 2 M KCl, 80 mM MOPS and 100 μM EDTA at pH 8.4 in both chambers.

FIG. 3 illustrates the interaction of arsenicals with the $P_{SH}$ pore under conditions similar to those used in FIG. 2, according to embodiments of the present invention.

FIG. 5 illustrates a 0.5 second current trace of stochastic sensing using a $P_{SH}$ pore, according to an embodiment of the present invention. 50 μM DTNB was used as the analyte and 50 μM DTT was present in the cis chamber. The transmembrane potential was −50 mV with 2 M KCl, 50 mM Tris.HCl and 100 μM EDTA at pH 8.5 in both chambers. The region of the current trace corresponding to the reaction of Cys-117 in the $P_{SH}$ pore with DTNB to form mixed disulfide 1 is labeled as "Step 1". The region corresponding to the reaction of the mixed disulfide (1) with DTT is to form unstable disulfide 2 is labeled as "Step 2". The region corresponding to the breakdown of unstable disulfide 2 to regenerate unbound $P_{SH}$ is labeled as "Step 3."

FIG. 8A illustrates $k_{3-obs}$ as a function of $[DTT]_{cis}$ in certain embodiments of the present invention. All measurements were for a 10 second interval at −50 mV with 2 M KCl, 30 mM MOPS, 100 μM EDTA at pH 8.5 in both chambers and 50 μM DTNB in the trans chamber. [DTT] is as indicated.

DETAILED DESCRIPTION

The present invention relates to methodologies of stochastic sensing in which the analyte covalently bonds to the sensor element. The sensor element may be an isolated or engineered protein pore, such as an ion channel. It may also be other engineered or isolated macromolecules such as proteins, oligonucleotides, inorganic and organic host molecules and imprinted surfaces.

Additionally, a variety of signals and bonding detection procedures may be used. Signals include conductance, fluorescence, force and any other effects of analyte binding to the chosen sensor element. These signals may be detected using electrical and optical measurements, force measurements, chemical techniques and any combination of the above.

Analytes may be reactive chemicals that covalently bond to the sensor element under the stochastic sensing conditions. Covalent bonds may be reversible or irreversible. The analytes may be any type of chemical including toxins, environmental indicators, chemical process products or by-products and contaminants. Chemical warfare agents, which can be arsenicals, organophosphates, mustard gasses, etc. Chemicals in foodstuffs, such as onion and garlic, pesticides such as organophosphates. Naturally occurring environmental toxins. Reactive pharmaceuticals. Many physiological molecules such as nitric oxide, endo and exo peroxides are extremely reactive messengers. Potential analytes that are not reactive are generally unable to covalently bond with the sensor element. Therefore, reactive and unreactive species of a similar chemical may be distinguished.

Analytes may covalently bond to the sensor element alone or in combination with a second molecule, such as a host or adaptor molecule. The analyte may covalently bond to the second molecule, which then covalently or non-covalently bonds to the sensor element or the second molecule may covalently bond to the analyte. Alternatively, the second molecule may simply affect the reaction kinetics of analyte bonding. If used to affect the reaction kinetics, the second molecule may be used to slow down or speed up rate of bonding or duration of the bound state to facilitate detection of the identity, concentration, or other properties of the analyte. The second molecule may also exert an effect on analyte bonding reaction kinetics by interacting with the analyte while not bound to the sensor element.

Other chemicals which act upon the bound analyte or are otherwise affected by the analyte/sensor element combination may also be added to the sensing system to augment sensing. For instance, the an analyte bound to an αHL pore that causes a change in ion flux, but is not easily distinguishable from another analyte by current trace may be distinguished by introduction of a chemical that cleaves one of the indistinguishable analytes, but not the other. Additionally, added chemicals may be used to further explore the chemical identity properties of the analyte using sensing methods other than the original sensor element. Such methods are used in exemplary embodiments with analytes that irreversibly bond to the sensor element.

Additionally, in stochastic sensing methodologies in which the analyte irreversibly covalently bonds to the sensor element, a chemical reagent may be added which breaks the covalent bond. The chemical reagent may exert this breaking effect through direct action on the bond or through indirect action such as binding to the analyte, an adapter molecule, or the sensor element. Such indirect action may result in a physical change of the analyte, adaptor or sensor element, such as a conformational change, or it may destroy the analyte or adapter. For example, the chemical reagent may actually be an enzyme that cleaves the analyte when it is bound to the sensor element.

The stochastic sensing methodology of the present invention may utilize a variety of physical arrangements. For example, systems using protein pore arrangements may have the pore embedded in a membrane, located between separate cis and trans chambers. It may be recommended to place the analyte in either the cis or the trans chamber exclusively, or the system may be readily functional regardless of the chamber in which the analyte is placed. The same is true for chamber placement of any adapter or chemical reagent for breaking of irreversible bonds. In most systems the chemical reagent will be placed in one chamber and the analyte in the other chamber. Other systems, such as those not relying upon electrical detection methods, may merely be a single chamber in which all elements of the system are combined.

It is also possible to prepare a sensing system in which portions of the system are introduced in a time-dependent manner or varied over time. For example, in a system for sensing an analyte that irreversibly bonds to the sensor element, a chemical reagent capable of breaking the bond may be introduced into the system only after irreversible bonding has occurred. It may even be removed after breaking the bond, for instance by replacing the solution on one side of a membrane.

In other embodiments the sample to be tested for analyte may be discharged and replaced over time. This may result from periodic introduction of new samples or by flowing a continuous stream of sample through the sensor. For example, a sensor system to detect the presence of a reactive chemical in industrial effluent may contain a chamber through which a small diverted stream of effluent flows. In such examples it may be necessary to regulate flow so that the sample remains in proximity with the sensor element for a sufficient amount of time to statistically allow detection of a particular analyte at or above a selected concentration.

The systems and methodologies of the present invention may be used in sensors for detection of various reactive molecules. These sensors may be fixed or portable and they may be designed for single-use applications or any number of multiple uses. Remote application sensors that may be placed or dropped in a target location and then transmit sensor information may also be used. Solutions or other chemicals for use in the sensors may be supplied with the sensors in a kit, or supplied independently for use with the sensors.

In certain embodiments of the present invention, an αHL protein pore may be embedded in a membrane which separates a cis chamber from a trans chamber. Interaction of the analyte, such as an organoarsenic compound, with the αHL blocks the of ions through the pore. This change in ion concentration in the cis and trans chambers modulates a current flow through a conductor connecting the two chambers. Measurement of this current to produce a current trace allows determination of when the analyte bonds with the αHL and when it becomes unbound.

When using the αHL pore, most analytes may be added to either the cis or the trans side, although analytes can more readily reach the pore from the trans side. The same is true for many adapters or chemical reagents for reversal of irreversible bonds.

The following examples are provided only to illustrate certain aspects of the invention and are not intended to embody the total scope of the invention or the totality of any aspect thereof. Variations of the exemplary embodiments of the invention below will be apparent to one skilled in the art and are intended to be included within the scope of the invention.

EXAMPLES

Example 1

Arsenic Compounds

Many arsenic compounds are poisonous and cause an array of serious to fatal disorders ranging from skin disease to cancer. Both man-made and artificial arsenic compounds are also problematic environmental contaminants. Arsenic compounds have also been made into chemical weapons. Stockpiles of one chemical weapon, Lewisite (2-chlorovinyldichloroarsine), are still in existence. Lewisite hydrolyzes in water resulting in a toxic arsenous acid that likely exerts its biological effects through reaction with thiols. 4-sulfophenylarsine oxide, an organoarsenic (III) reagent, reacts with thiols in a manner similar to Lewisite. Other organoarsenic compounds are also potential chemical weapons or environmental contaminants, or mimic the biological action of arsenic-based weapons and contaminants.

Sodium 4-sulfophenylarsonic acid used in these Examples was prepared by dissolving 7.62 g of Sulfanilic acid in 40 mL of water to create a 44 mmol solution also containing 2.8 g of sodium carbonate. Diazotization was performed by adding, simultaneously, 10 mL concentrated HCl and 40 mL of 46.6 mmol sodium nitrite solution (formed from 3.2 g sodium nitrite in 40 mL water) with two dropping funnels. The resulting solution, which contained some precipitate, was dropped into an ice-chilled 100 mL of solution of 100 mmol arsenic trioxide, 200 mmol sodium hydroxide, and 0.75 mmol copper sulfate (formed from adding 9.82 g arsenic trioxide, 8.08 g sodium hydroxide, and 120 mg copper sulfate to 100 mL water). The color of the solution changed from blue to dark green and large amounts of $N_2$ gas were released. After three days at room temperature, the volume was reduced to approximately 25 mL with a rotary evaporator. A precipitate was removed by filtration. The filtrate was boiled briefly, then acidified with concentrated HCl resulting in an immediate precipitate. After 4 days at room temperature, the solid was collected by filtration and washed in turn with saturated KCl, 80% ethanol, then acetone. After drying under a vacuum, a 5.21 g of a light brown solid was recovered. NMR analysis showed the following results: $^1$H NMR 300 MHz ($D_2O$):8.03 (d, 2H,J=8.4 Hz), 7.97(d,2H,J=8.7 Hz).

Sodium 4-sulfophenyldiiodoarsine used in these Examples was formed by adding 3 mL of 57% hydroiodic acid in water to 10 mL of a 55-60° C. solution of 3.39 mmol sodium 4-sulfophenylarsonic acid (formed by solubilizing 1.03 g in 10 mL water). After 5 minutes, the dark solution was cooled on ice and the precipitated solid was collected and washed with acetic acid, followed by acetone. The bright yellow solid was dried under vacuum. It weighted 1.05 g (61% yield). This crude product was recrystallized from 80% acetic acid, yielding yellow needles. The $^1$H NMR spectrum in $D_2O$ showed that sodium p-sulfophenyldiiodoarsine is hydrolyzed to sodium 4-sulfophenylarsine oxide. $^1$H NMR 300 MHz ($D_2O$):7.88(d, 2H,J=8.7 Hz), 7.84(d,2H,J=8.4 Hz). HRMS (of hydrolysis) calculated for $C_6H_4O_4SAs$ (M$^-$) 246.9046 found 246.9041. Microanalysis (Atlantic Microlab, Inc.) calculated for $C_6H_4O_3I_2SAsNa$; C:14.19, H:0.79, 0:9.45, I:49.97, S:6.31, found C:15.33, H:1.13, O:10.90, I:49.54, S:5.79. A microanalysis after additional recrystallization also suggested that the crystals retained solvent or that slight hydrolysis of the diiodide occurred.

4-aminophenylarsine oxide used in these Examples was formed by adding 10.9 g of p-Arsanilic acid to a solution 30 mL methanol, 24 mL concentrated hydrochloric acid, and 100 mg potassium iodide. Sulfur dioxide was bubbled into the solution for 25 minutes at room temperature. The color of the solution changed from bright brown to white, followed by precipitation of 4-aminophenyldichloroarsine as the HCl salt. The mixture was cooled in an ice bath and the precipitate was collected and washed with dry ethyl ether. 500 mg of the precipitate was dissolved in 65 mL of 10% ammonium hydroxide. 4-aminophenylarsine oxide slowly precipitated overnight at room temperature. The product was collected, washed with diethyl ether and dried in a vacuum. A white solid (325 mg) was recovered. Microanalysis (Atlantic Microlab, Inc.) calculated for $C_6H_6NOAs$; C:39.37, H:3.30, N:7.65, O:8.74 found C:39.44, H:3.21, N:7.73, O:8.83.

Arsenite solutions used in these Examples were formed by dissolving 100 mM sodium metaarsenite in water.

Arsenate solutions used in these Examples were formed by dissolving 100 mM arsenic acid in water.

Dimethylarsinate solutions used in these Examples were formed by dissolving 100 mM cacodylic acid, sodium salt in water.

Phenylarsine oxide solutions used in these Examples were formed by dissolving phenylarsine oxide at 1 mM in DMSO. This solution was diluted with water for make a 100 μM stock.

4-sulfophenylarsine oxide solutions used in these Examples were formed by dissolving 100 mM 4-sulfophenylarsine in water with adjustment to pH 7 using 1 M sodium hydroxide.

4-aminophenylarsine oxide solutions used in these Examples were formed by dissolving 4-aminophenylarsine in 50 mM MES at pH 5.5 (titrated with HCl) to make a 1 mM solution.

DTT solutions used in these Examples were formed from preweighed samples of sold D,L-DTT stored at −20° C. At the time of the experiment, buffer was added to the sample in a tube to generate a stock of 1M DTT, which was kept on ice. Fresh stock solutions of DTT were prepared every 2 hours.

DTNB solutions used in these Examples were formed from 100 mM DTNB dissolved in 200 mM Na phosphate, pH 8.5. This stock solution was diluted as necessary. Because DTNB decomposes in basic solution, fresh DTNB stocks were made daily.

Example 2

Preparation of the PSH αHL Pore Protein

The $P_{SH}$ variant of the αHL pore contains a Cys-117 mutation, in which Cys replaces the usual Thr. This places the thiol side chain of Cys projecting into the lumen of the αHL pore. To prepare $P_{SH}$ pores, first [$^{35}$S] Met labeled monomeric polypeptides were prepared by in vitro transcription and translation (IVTT). These monomeric IVTT products were used to make the αHL heptamers.

50 μL of a 50 μg/mL solution of wild-type-like αHL (RL2) were mixed with 20 μL of a 50 μg/mL mutated αHL (T117C-D8) solution 30 μL of a suspension of rabbit red blood cell membranes (at 3 mg membrane protein/mL) was diluted with 500 μL MBSA (10 mM MOPS, 150 mM NaCl, pH 7.4, titrated with HCl). The membranes were centrifuged for 5 minutes at 21,000×g and the supernatant was removed. The washed membranes were then resuspended with the protein mixture. After 70 minutes at 37° C., the membranes were pelleted by centrifugation for 5 minutes at 21,000×g and resuspended in 100 μL of MBSA containing 2 mM DTT. The membranes were then recovered again by centrifugation.

The washed membrane pellet containing the assembled heptamers was solubilized in 50 μL of sample buffer and loaded into one lane of a 5% SDS polyacrylamide gel, which was run at 30V overnight. The D8 ($Asp_8$) tail allowed the separation of heptamers with different combinations of mutated αHL subunits. The gel was dried at 50° C. for 4 hours and then exposed to X-ray film for 2 hours. The band corresponding to $P_{SH}$ (a heptamer with 6 wild-type-like monomers and one mutant monomer) was excised.

The excised gel portion was then hydrated in 400 μL of 10 mM Tris.HCl, pH 7.5 containing 2 mM DTT and the paper was removed. The gel was then crushed using a plastic pestle and the resulting suspension was rotated at 4° C. overnight. The material was then filtered through a 0.2 μM cellulose acetate filter. The filtrate, which contained $P_{SH}$ was stored at −80° C.

Although the example above is intended for small-scale preparations of αHL sensor elements and includes radioactivity, which may be unwanted in industrial applications, the large-scale production and assembly of complex proteins without the use of radioactivity or other hazardous materials is well known in the art. Accordingly, one skilled in the art should be able to produce commercial scale batches of the αHL pore with little difficultly.

For example, wild-type-like and mutated portion of the pore may be grown separately in bioreactors and purified then combined in proportions similar to those described above to produce self-assembled pores.

Example 3

Electrophysiology Apparatus

Experiments using αHL pores in these Examples were carried out using folded bilayer membranes. To prepare such membranes, a 25 μm thick Teflon septum was clamped between two Teflon chambers each of 1 mL volume. A bilayer was formed on a 100 μm diameter aperture in the septum. The septum was pretreated with 10% (v/v) hexadecane in highly purified n-pentane. Both chambers contained an electrolyte solution containing 2M KCl, 100 μM EDTA and a selected amount of MOPS, Tris or another buffer.

Initially the chambers were filled with electrolyte to a level slightly below the aperture. A bilayer material 1% (w/v) 1,2-diphytanoyl-sn-glycerophosphocholine in 6 μL pentane was spread on the surface of each chamber. After about 3 minutes, during which time the pentane solvent in the bilayer material evaporated, the electrolyte level in each chamber was raised above the aperture. The formation of a bilayer was monitored by observing the increase in membrane capacitance to a value of approximately 130 pF.

A single αHL pore was inserted into the bilayer by adding a solution of the pore to the cis chamber to produce a final concentration of about 0.5 ng/mL. The cis chamber, which was kept at ground, was stirred until electrical recordings indicated that a single protein channel appeared in the bilayer.

The test arsenical or arsenicals were added to the trans chamber. Electrical current disruption from blocking of the αHL pore upon arsenical binding was detected through two Ag/AgCl electrodes and amplified with a patch-clamp amplifier (Axopatch 200B; Axon Instruments, Union City, Calif.), filtered with a low-pass Bessel filter (80 dB/decade) with a corner frequency of 1 kHz, and then digitized with a DigiData 1200 A/D/ converter (Axon Instruments) at a sampling frequency of 5 kHz. Data samples were stored electronically and then current traces were filtered digitally at 100 Hz for further analysis and display. Event data files used to generate dwell-time (durations of various states of the pore) histograms were constructed using the Fetchan program (Axon Instruments). Processed data were plotted using Origin 6.1 (OriginLab Corp., Northampton, Mass.). Individual values were presented as the mean +/− standard deviation.

Example 4

Interaction of 4-sulfophenylarsine oxide with $P_{SH}$

Figure 2A:
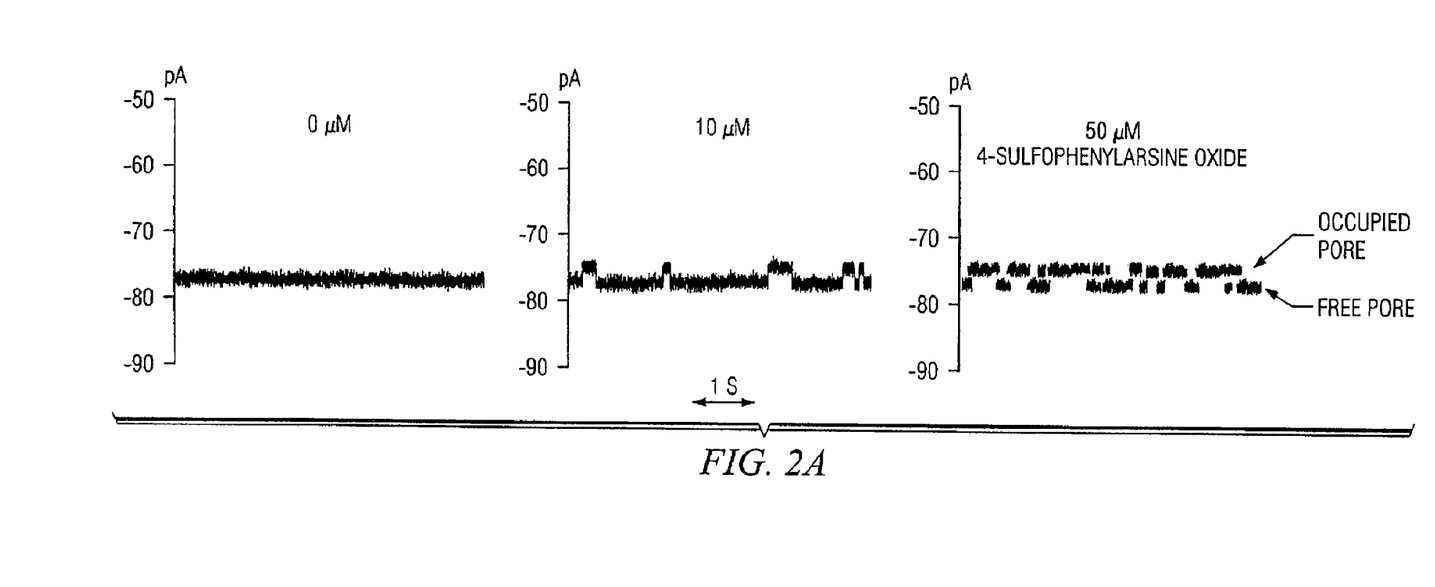
FIG. 2A shows current traces in the presence of 0, 10 and 50 μM 4-sulfophenylarsine oxide in the trans chamber. Current levels of the unoccupied and occupied pore are indicated in the figure.

The interaction of $P_{SH}$ with 4-sulfophenylarsine oxide was examined by single-channel electrical recording. In the absence of 4-sulfophenylarsine oxide $P_{SH}$ produced a quiet single channel current of 1.54+/−0.03 nS (n=7) (See FIG. 2A.) In the presence of both 10 μM and 50 μM 4-sulfophenylarsine oxide, steps were observed in which the current was reduced to 1.49+/−0.04 nS (n=7). (See FIG. 2A.) The steps had a mean duration of 702+/−38 msec (n=6) and represent individual couplings of 4-sulfophenylarsine oxide to the Cys residue in the $P_{SH}$ pore. As FIG. 2A shows, an increase in 4-sulfophenylarsine oxide concentration also resulted in an increase in the frequency of such couplings.

These events were not observed when 4-sulfophenylarsine oxide was added to a bilayer containing a completely wild type αHL pore, which contains no lumen Cys residues. Additionally, the coupling events were eliminated by either replacing the arsenical solution with buffer or by the addition of 1.5 mM BAL to 10 μM arsenical. BAL is a dithiol which is know to react with $As^{III}$ compounds and therefore was expected at sufficient concentration to react with all available arsenical and prevent its bonding to the $P_{SH}$ pore.

Figure 2B:
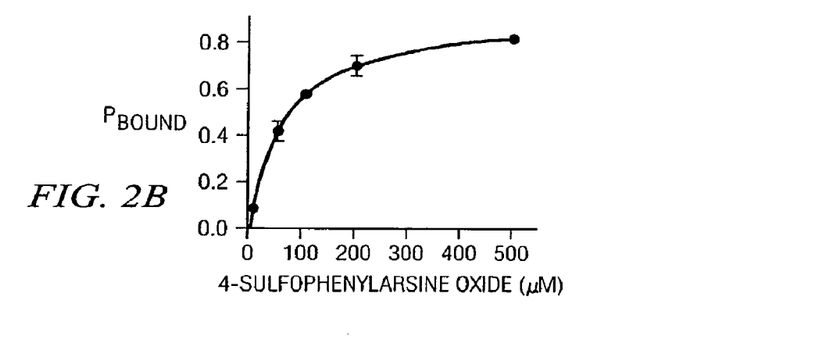
FIG. 2B is a plot of $P_{bound}$ (probability that the arsenical is attached to the pore) versus concentration of 4-sulfophenylarsine oxide.

FIG. 2B was constructed using data obtained as described above for various concentrations of 4-sulfophenylarsine oxide. $P_{bound}$ is the probability that a molecule of the arsenical is attached to the pore. The increase of $P_{bound}$ with arsenical concentration indicates that the reaction frequency does increase with increasing arsenical concentration.

Figure 2C:
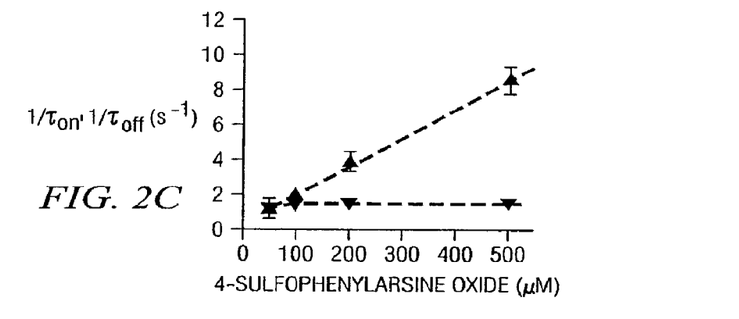
FIG. 2C plots the reciprocal of the mean residence time ($\tau_{off}$) and the mean inter-event intervals ($\tau_{on}$) versus 4-sulfophenylarsine oxide concentration. Values of $\tau_{off}$ and $\tau_{on}$ were obtained by fitting dwell-time histograms to single exponential functions. $1/\tau_{off}$ is represented with downward-pointing triangles. $1/\tau_{on}$ is represented with upward-pointing triangles.
Figure 3A:
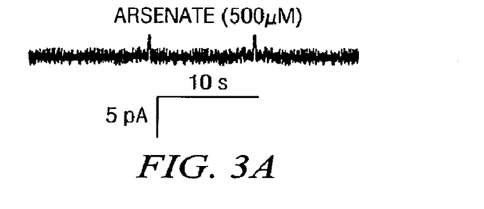
FIG. 3A is a 10 second current trace using 500 μM arsenate.
Figure 3B:
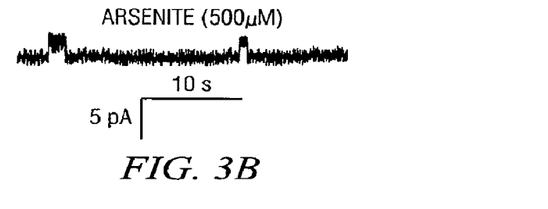
FIG. 3B is a 10 second current trace using 500 μM arsenite.
Figure 3C:
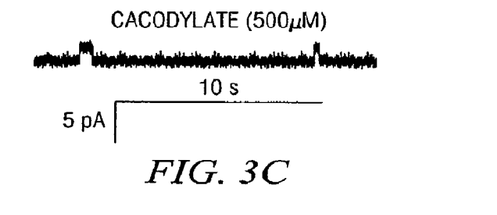
FIG. 3C is a 10 second current trace using 500 μM cacodylate.
Figure 3D:
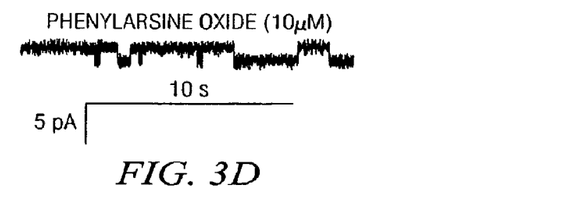
FIG. 3D is a 10 second current trace using 10 μM phenylarsine oxide.

FIG. 2C was also constructed using data obtained as described above for various concentrations of 4-sulfophenylarsine oxide. $\tau_{off}$ represents the mean residence time of the arsenical in the pore. $\tau_{on}$ is the mean inter-event (arsenical-pore coupling) interval. The association constant ($k_{on}$) for the analyte/pore coupling is $1/\tau_{on}[A]$ where [A] is the concentration of analyte, in this case 4-sulfophenylarsine oxide. Accordingly, the constant relationship of $1/\tau_{on}$ with [A], as shown in FIG. 2C by the line with upward pointing triangles, indicates that the rate of pore coupling correlates in a linear fashion with the concentration of analyte. This is consistent with a simple bimolecular interaction where concentration of one molecule (the pore) is held constant. In such an instance, the rate at which the interaction occurs should increase linearly with the concentration of the other molecule (the analyte). $k_{on}$ is the slope of the line. For the interaction of 4-sulfophenylarsine oxide with $P_{SH}$, $k_{on}$ was calculated to be $20+/-3\times10^3$ M$^{-1}$s$^{-1}$.

The dissociation constant ($k_{off}$) for the analyte/pore coupling is $1/\tau_{off}$ is shown by the line with downward pointing triangles in FIG. 2C. Because $k_{off}$ in a unimolecular interaction is not influenced by concentrations of the molecules, but rather by the nature of the interaction, one would expect it to remain essentially constant despite changing analyte concentration. FIG. 2C shows just this effect. For the interaction of 4-sulfophenylarsine oxide with $P_{SH}$, $k_{off}$ was calculated to be $1.4+/-0.1$ s$^{-1}$.

The dissociation constant for the interaction, $K_d$, which indicates the overall strength of the interaction and how easily the bimolecular complex can be separated, is $75+/-15\times10^{-6}$ M at 24° C. (n=4). $K_d$=dissociation rate ($k_{off}$)/association rate ($k_{on}$). Accordingly, lower $K_d$ values indicate stronger binding.

Example 5

Interaction of Various Arsenicals with $P_{SH}$

The interaction of $P_{SH}$ with various other arsenicals was examined by single-channel electrical recording. In the absence of arsenicals $P_{SH}$ produced a quiet single channel current (See FIG. 3.) In the presence of 500 μM arsenate, arsenite, or cacodylate or 10 μM phenylarsine oxide steps were observed in which the current was reduced. (See FIGS. 3A-D, respectively.) The amplitudes of current reduction and mean dwell times varied depending upon the arsenical. This indicates that different arsenicals result in detectably different signals when bound to the $P_{SH}$ pore. Therefore, it is possible to sort signals from the binding of different arsenicals with a $P_{SH}$ pore to determine individual arsenical identity and concentration even if the arsenicals are mixed in a solution.

Example 6

Reaction Mechanism for Reversal of an Irreversible Covalent Interaction

Figure 4:
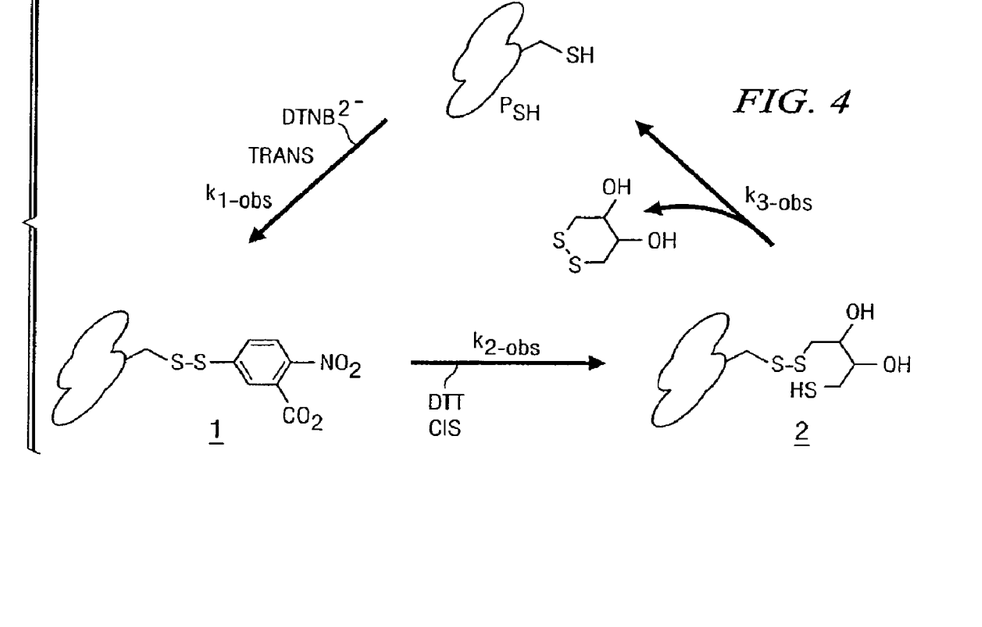
FIG. 4 illustrates the chemical reaction cycle of certain embodiments of the present invention in which DTT is used as a chemical reagent to reverse an irreversible covalent bond between the $P_{SH}$ pore and DTNB. Specifically, Cys-117 reacts with DTNB in a bimolecular reaction, with a rate constant $k_{1-obs}$ to form a mixed disulfide (1) ("Step 1"). Disulfide 1 then reacts with D,L-DTT in a second biomolecular reaction, with a rate constant $k_{2-obs}$, to form an unstable disulfide 2 ("Step 2"), which breaks down in a unimolecular reaction, with a rate constant $k_{3-obs}$, in which $P_{SH}$ is regenerated ("Step 3").

The $P_{SH}$ αHL pore may also be used to investigate the interaction of non-arsenical compound with Cys-117. For example, DTNB forms a disulfide bond with Cys-117. DTNB is a non-arsenical model reactive analyte. This bond between DTNB and the pore is irreversible, but may be cleaved by DTT to regenerate the Cys residue and open the pore. In the overall reaction, (diagrammed in FIG. 4) Cys-117 in the lumen of the pore reacts with DTNB in a bimolecular reaction ("Step 1") with rate constant $k_{1-obs}$ to form a mixed disulfide 1. In mixed disulfide 1 the sulfur atom proximal to the protein wall is activated for reaction with free thiolates because the aromatic thiolate is a good leaving group. Therefore, mixed disulfide 1 reacts with DTT in a bimolecular reaction ("Step 2") with a rate constant $k_{2-obs}$ to form an unstable disulfide 2. Unstable disulfide 2 breaks down in a unimolecular reaction with rate constant $k_{3-obs}$ in which $P_{SH}$ is regenerated. As a result, $P_{SH}$ is able to undergo multiple cycles of reaction.

Figure 5:
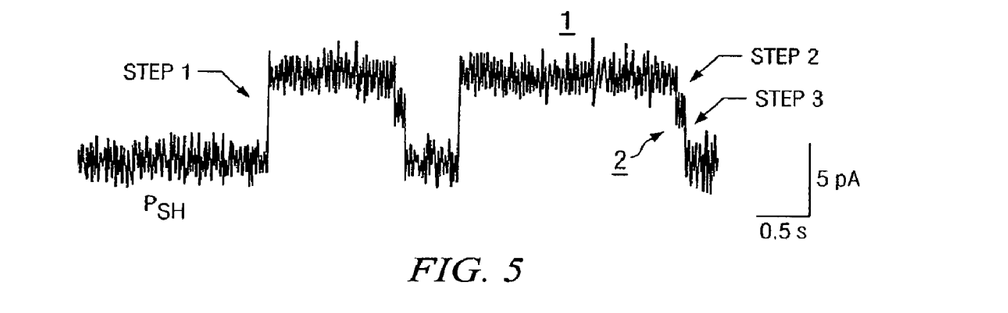

The steps of the above reaction are clearly visible in a current trace of a single pore system. To produce the current trace of FIG. 5, a $P_{SH}$ pore in a bilayer membrane was prepared as described in the previous examples. DTNB was added to the trans chamber and DTT was added to the cis chamber. In the single channel recording shown, three separate current levels representing unbound $P_{SH}$, mixed disulfide 1 and unstable disulfide 2 were observed. The current trace at Step 3 is consistent with the existence and unimolecular breakdown of unstable disulfide 2.

Example 7

Kinetics of the Interaction of DTNB, DTT and $P_{SH}$

Figure 6A:
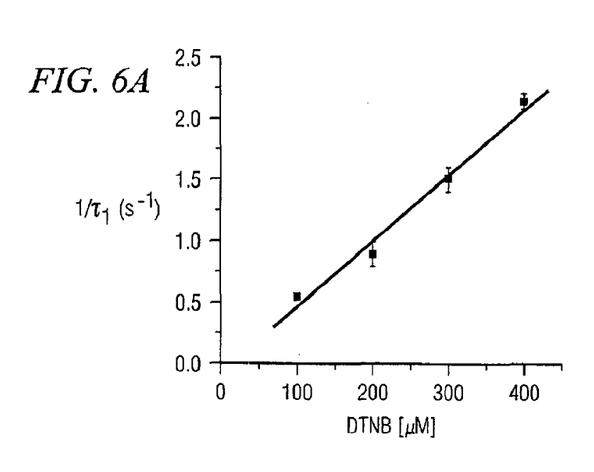
FIG. 6A illustrates the dependence of $1/\tau_1$ on $[DTNB]_{trans}$, where $\tau_1$ is the time interval between Step 3 and Step 1 during the interaction of DTNB and DTT with a $P_{SH}$ pore (i.e. the lifetime of free $P_{SH}$ before the bonding of DTNB), according to certain embodiments of the present invention. The data were obtained using the indicated concentrations of DTNB on the trans side of the pore. All measurements were for a 10 second interval at −50 mV with 2 M KCl, 30 mM MOPS, 100 μM EDTA at pH 8.5 in both chambers and and 50 μM DTT in the cis chamber. The current level corresponding to a single, unmodified pore was −82.2+/−2.1 pA. $k_{1-obs}$ was obtained from the slope of the straight fit line as illustrated.

The rate of reaction of DTNB with Cys-117 of $P_{SH}$ was measured with DTNB in the trans chamber and 50 μM DTT in the cis chamber at an applied potential of −50 mV with a solution of 2 M KCl, 30 mM MOPS and 100 μM EDTA, pH 8.5 in both chambers. Because the reaction of DTNB with $P_{SH}$ is a bimolecular reaction and the concentration of $P_{SH}$ is constant, the reaction rate, $k_{1-obs}$ is constant and may be calculated as $1/\tau_1$[DTNB], where $\tau_1$ is the mean amount of time $P_{SH}$ remains unbound in the presence of DTNB. As FIG. 6A illustrates, there is a linear relationship between [DTNB] and $1/\tau_1$, consistent with the assumption that the reaction is bimolecular. Using the data of FIG. 6A, $k_{1-obs}$ was calculated to be $4.9+/-0.5\times10^3$ M$^{-1}$s$^{-1}$ (n=5).

Figure 6B:
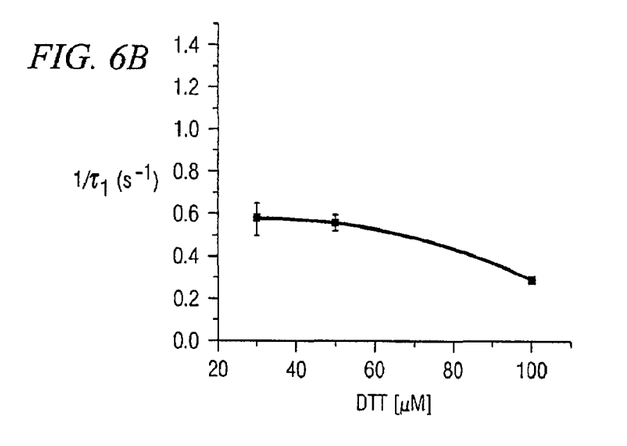
FIG. 6B illustrates the effects of various concentrations of DTT of the cis side of a $P_{SH}$ pore, according to certain embodiments of the present invention. Measurements were made using the system described for FIG. 6A, but with 100 μM DTNB and varying concentrations of DTT. The effects of DTT concentration on $1/\tau_1$ are indicated.

In the system described above, it was uncertain whether DTT might leak from the cis side of the chamber to the trans side and react there with DTNB, thereby reducing the concentration of DTNB available to interact with $P_{SH}$ and producing inaccurate DTNB concentration measurements using the system. FIG. 6B illustrates that at concentrations of DTT below approximately 60 μM, the rate constant for the interaction of DTNB with $P_{SH}$ is not significantly affected. At DTT concentrations below approximately 40 μM the effect is nearly unnoticeable.

Figure 7A:
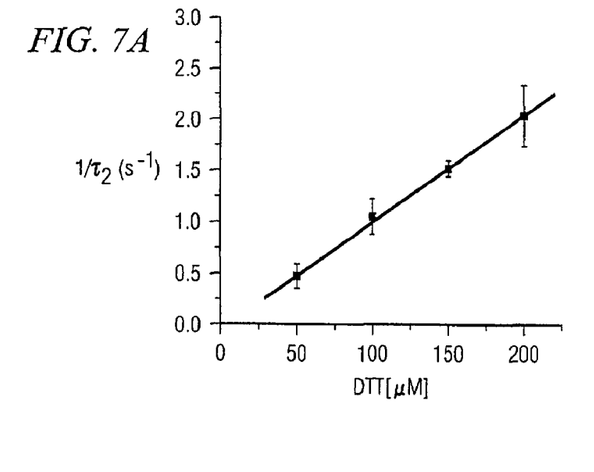
FIG. 7A illustrates the dependence of $1/\tau_2$ on $[DTT]_{trans}$, where $\tau_2$ is the time interval between Step 1 and Step 2 during the interaction of DTNB and DTT with a $P_{SH}$ pore (i.e. the lifetime of the state with DTNB covalently bound to $P_{SH}$ as a mixed disulfide 1 and the reaction of the mixed disulfide 1 with DTT), according to certain embodiments of the present invention. The data were obtained using the indicated concentrations of DTT on the trans side of the pore. All measurements were for a 10 second interval at −50 mV with 2 M KCl, 30 mM MOPS, 100 μM EDTA at pH 8.5 in both chambers and 50 μM DTNB in the cis chamber. $k_{2-obs}$ was obtained from the slope of the straight fit line as illustrated.
Figure 7B:
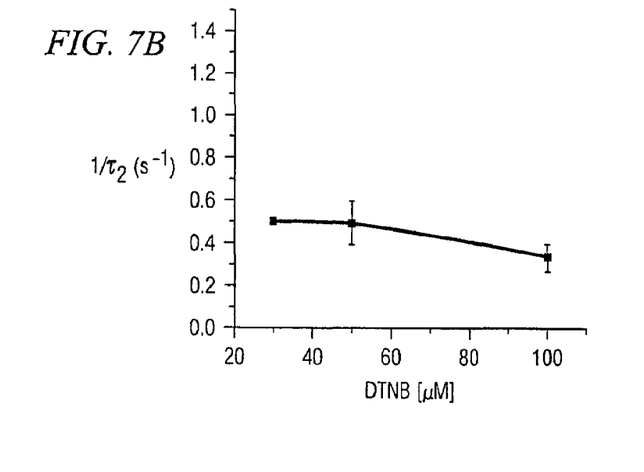
FIG. 7B illustrates the effects of various concentrations of DTNB on the cis side of a $P_{SH}$ pore, according to certain embodiments of the present invention. Measurements were made using the system described for FIG. 7A, but with 50 μM DTT and varying concentrations of DTNB. The effects of DTNB concentration on $1/\tau_2$ are indicated.

Similarly, it was plausible that the reaction rate of DTT with mixed disulfide 1 to form unstable disulfide 2 and ultimately free the $P_{SH}$ pore might be influenced by the rate of diffusion of DTT from the cis chamber through the pore. This rate might be decreased by the movement of DTNB from the trans chamber to the cis chamber, where it would interact with DTT and thereby deplete DTT levels. To investigate the possibility of this event, a reverse arrangement from that described above was used with 50 μM DTNB on the cis side of the membrane and DTT on the trans side. Because of the shape of the αHL pore, from the trans side chemicals have free access to the lumen, but are considerably more restricted from the cis side. Because the interaction of DTT with the DTNB/$P_{SH}$ complex is a bimolecular interaction with a constant concentration of DTNB/$P_{SH}$, the rate constant, $k_{2-obs}$ is equal to $1/\tau_2$ [DTT], where $\tau_2$ is the length of time between binding of DTNB to $P_{SH}$ and the beginning of Step 2. As FIG. 7A illustrates, there is a linear relationship between [DTT] and $1/\tau_2$, consistent with the assumption that the reaction is bimolecular. Using the data of FIG. 7A, $k_{2-obs}$ was calculated to be $1.1+/-0.1\times10^4$ M$^{-1}$s$^{-1}$. Additionally, FIG. 7B illustrates that, in fact, at low concentrations of [DTNB] in the cis chamber the lifetime of mixed disulfide 1 is not affected. In particular, at concentrations below 60 μM little effect is observed and below 40 μM almost no detectable effect can be seen. This confirms that movement of DTNB from the cis chamber to the trans chamber is minimal at low concentrations.

Figure 8A:
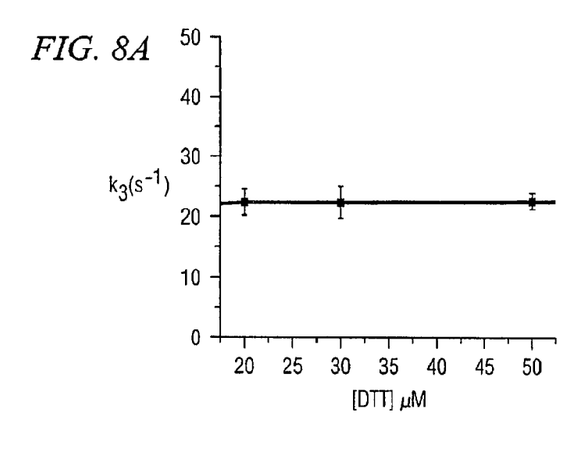
Figure 8B:
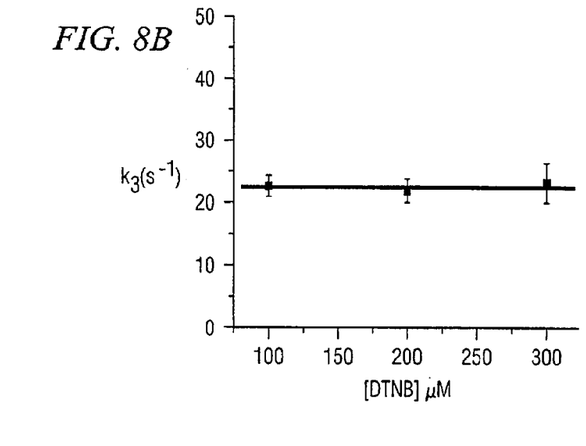
FIG. 8B illustrates $k_{3-obs}$ as a function of $[DTNB]_{trans}$ in certain embodiments of the present invention. All measurements were for a 10 second interval at −50 mV with 2 M KCl, 30 mM MOPS, 100 μM EDTA at pH 8.5 in both chambers and 50 μM DTT in the cis chamber. [DTNB] is as indicated.

The breakdown of unstable mixed disulfide 2 is a unimolecular reaction. Therefore, $k_{3-obs}=1/\tau_3$, where $\tau_3$ is the time between formation of the mixed disulfide 2 at the end of Step 2 and its breakdown at the end of Step 3. To illustrate the unimolecular nature of Step 3 and determine $k_{3-obs}$, DTNB was added to the trans chamber of a single pore system while DTT was added to the cis chamber. A solution of 2 M KCl, 30 mM MOPS and 100 μM EDTA at pH 8.5 was used in both chambers and the applied potential was −50 mV. In the tests depicted in FIG. 8A, the concentration of DTNB was held constant at 50 µM while concentration of DTT was varied as shown. The linear relationship of $k_{3-obs}$ with [DTT] is apparent in the figure. Similarly, in FIG. 8B, test were performed with the concentration of DTT fixed at 50 µM while the concentration of DTNB was varied as shown. The linear relationship of $k_{3-obs}$ with [DTNB] is apparent in the figure. In both tests, $k_{3-obs}$ was calculated to be $23+/-1$ $s^{-1}$.

Figure 9:
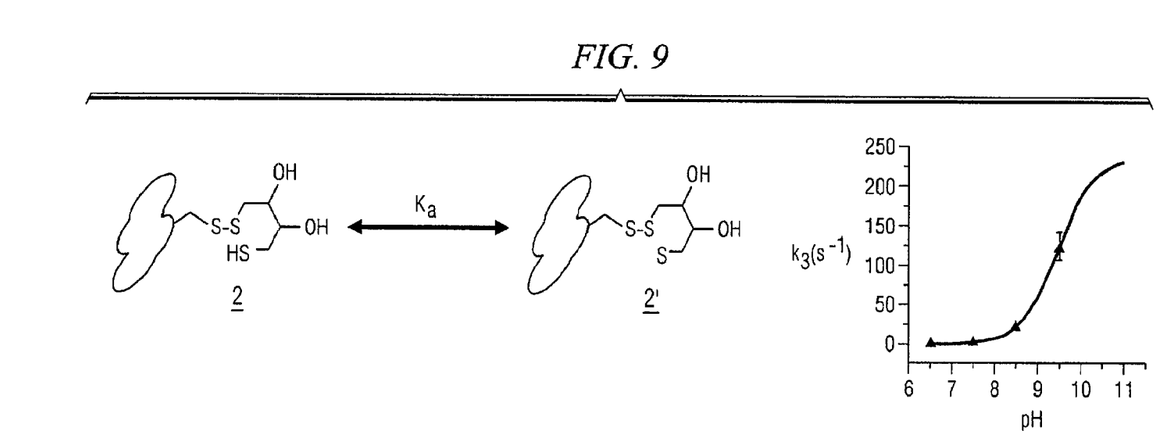
FIG. 9 illustrates the pH dependence of the rate of breakdown of the unstable disulfide 2 formed during the interaction of DTNB, DTT and the $P_{SH}$ pore, according to certain embodiments of the present invention. 50 μM DTNB was used as the analyte in the trans chamber and 50 μM DTT was present in the cis chamber. The transmembrane potential was −50 mV with 2 M KCl, 30 mM MOPS and 100 μM EDTA. pH in both chambers is as indicated. $k_{3\text{-}obs}$ is shown as a function of pH. The data were fitted to $k_{3\text{-}obs}=(k_3 K_a)/(K_a+[H^+])$.

To verify that the intermediate unstable disulfide 2 was formed from DTT, several control experiments were performed. In addition, the intermediate structures of unstable disulfide 2 were investigated at various pH values. A plot of $k_{3-obs}$ as a function of pH is shown in FIG. 9. The data related to the plot could be fitted to the equation $k_{3-obs}=(k_3 K_a)/(K_a+[H^+])$. This suggests that the reactive form of 2 is a thiolate. The data indicate that the $pK_a$ of 2 is $9.5+/-0.2$ and $_{K3}$ is $250+/-80$ $s^{-1}$ in the deprotonated form. In comparison, the first $PK_a$ of DTT is 9.2 and the $pK_a$ of mercaptoethanol is 9.5.

Example 8

Interaction of MTSES, DTT and $P_{SH}$

Figure 10:
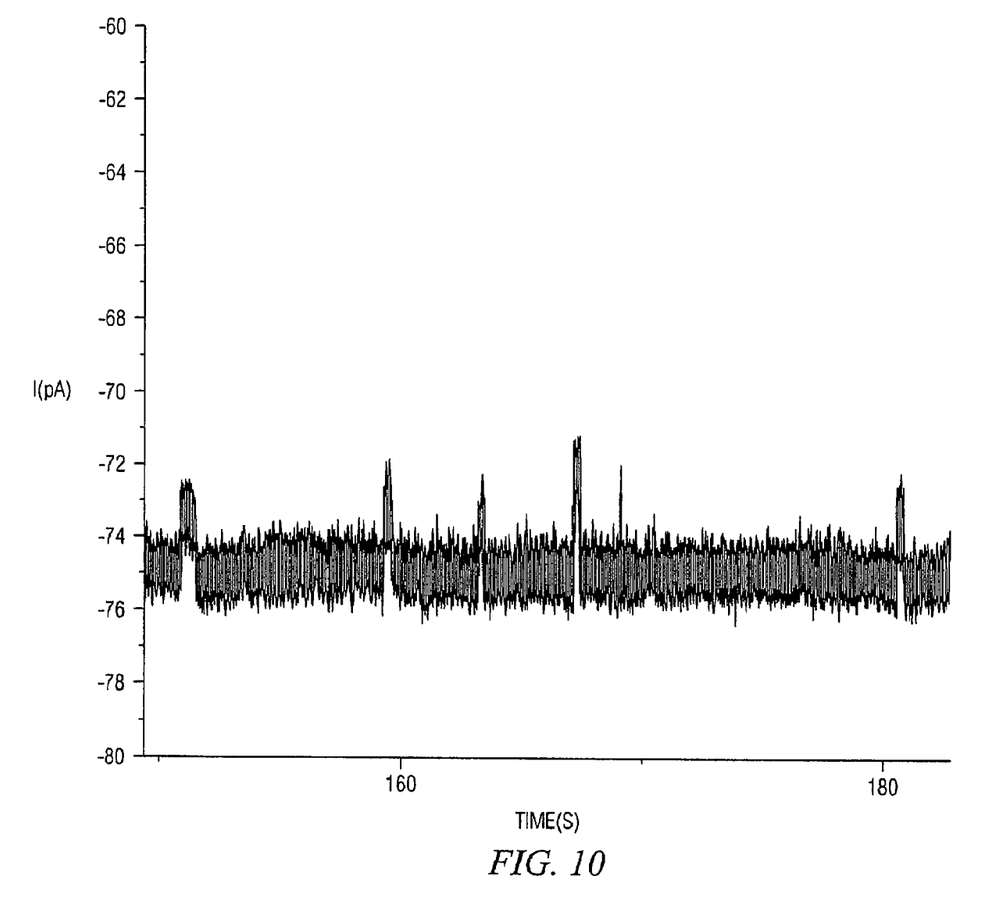
FIG. 10 illustrates a 30 second current trace of stochastic sensing using a $P_{SH}$ pore, according to an embodiment of the present invention. 2.5 mM MTSES was used as the analyte in the trans chamber and DTT was present in the cis chamber. The transmembrane potential was −50 mV with 2 M KCl, 50 mM Tris.HCl and 100 μM EDTA at pH 8.5 in both chambers.

A single pore system as described above was prepared and supplied with a solution of 2 M KCl, 50 mM Tris.HCl and 100 µM EDTA at pH 8.5 in both chambers. 50 µM DTT was supplied to the cis chamber. 2.5 mM MTSES was provided in the trans chamber. A transmembrane potential of −50 mV was applied. As shown in FIG. 10, MTSES bound to the $P_{SH}$ pore, thereby blocking it. Interaction of DTT with MTSES broke the irreversible disulfide bond and opened the $P_{SH}$ pore.

Example 9

Other Engineered Pores and Alternative Systems

The above examples indicate that the conditions inside the $P_{SH}$ pore at least approximate the conditions in solution. In order to mimic solution conditions even more closely, additional mutations may be made to the wild-type αHL monomer. For example, hydrophobic side chains in the channel may be may be replaced with hydrophilic side chains such as Ser, Thr, Asn and Gln. Surface charge effects in the pore can also be minimized by using high salt concentrations, as in these examples.

Other sensors may be used in the present invention that do not require solution conditions within a pore or other area to function well.

The αHL system described above may also be used to study the effects of protein environment on chemistry. Residues that bind substrates or take part in the chemistry may be introduced onto on the wall of the channel by mutagenesis, targeted chemical modification of non-natural amino acid substitution. For example, histidine residues may be used for catalysis. Through selected substitutions, it may be possible to improve turnover rates or couple catalysis transmembrane transport.

All of the systems and/or methods disclosed and claimed herein can be made and executed without undue experimentation in light of the present disclosure. While the systems and methods of this invention have been described in terms of specific embodiments, it will be apparent to those of skill in the art that variations may be applied to the systems and/or methods and in the steps or in the sequence of steps of the methods described herein without departing from the concept, spirit and scope of the invention. All such similar substitutes and modifications apparent to those skilled in the art are deemed to be within the spirit, scope and concept of the invention.

What is claimed is:

1. A method for sensing an individual molecule of at least one reactive analyte in a solution comprising:
   providing a sensing device separated into a trans chamber and a cis chamber by a divider, wherein an engineered protein pore is operably disposed in the divider;
   providing a detection system operable to detect a current between the cis and trans chambers;
   providing an ionic solution containing at least one reactive analyte capable of covalently bonding to the protein pore within the lumen of the pore and thereby altering the current between the cis and trans chambers to the cis or trans chamber; and
   detecting the current between the cis and trans chambers, wherein a change in the current between the cis and trans chambers indicates whether the analyte is covalently bound to the protein pore; and
   using the detected current, stochastically sensing the at least one analyte.

2. The method of claim 1, wherein the pore is an αHL pore comprising at least one monomer having a Cys residue at amino acid 117.

3. The method of claim 1, wherein the reactive analyte is selected from the group consisting of: chemical weapons, environmental toxins and pharmaceuticals.

4. The method of claim 1, wherein the reactive analyte comprises an arsenical.

5. The method of claim 1, wherein the reactive analyte irreversibly covalently bonds to the protein pore, further comprising providing to the cis or trans chamber an ionic solution containing a chemical reagent capable of breaking the covalent bond.

6. The method of claim 5, wherein the reactive analyte and chemical reagent are provided to separate chambers.

7. The method of claim 1, wherein the ionic solution comprises a plurality of species of chemically distinct reactive analytes capable of covalently bonding with the protein pore to produce distinct current signals.

8. The method of claim 7, further comprising analyzing the detected current between the cis and trans chambers for the distinct current signals.

9. The method of claim 1, further comprising determining the identity and concentration of at least one reactive analyte based upon the detected current between the cis and trans chambers.

10. The method of claim 1, wherein the reactive analyte irreversibly covalently bonds to the protein pore, further comprising providing a chemical capable of reacting with the analyte to produce a second signal.

11. A method for sensing an individual molecule of at least one reactive analyte in a solution comprising:
   introducing an ionic solution containing at least one reactive analyte capable of covalently bonding to an engineered protein pore within the lumen of the pore into a sensing device comprising a trans chamber and a cis chamber separated by a divider, wherein the divider comprises the engineered protein pore operably disposed therein;
   detecting a change in current between the cis and trans chambers, wherein the change in the current between the cis and trans chambers indicates whether the analyte is covalently bound to the protein pore;
   using the change in detected current to sense an individual molecule of the reactive analyte.

12. The method of claim 11, wherein the pore is an αHL pore comprising at least one monomer having a Cys residue at amino acid 117.

13. The method of claim 11, wherein the reactive analyte is selected from the group consisting of: chemical weapons, environmental toxins and pharmaceuticals.

14. The method of claim 11, wherein the reactive analyte comprises an arsenical.

15. The method of claim 11, wherein the reactive analyte irreversibly covalently bonds to the protein pore, further comprising breaking the covalent bond using a chemical reagent.

16. The method of claim 15, further comprising placing the reactive analyte in one of the cis or trans chambers and placing the chemical reagent in the other chamber.

17. The method of claim 11, wherein the ionic solution comprises a plurality of species of chemically distinct reactive analytes capable of covalently bonding with the protein pore to produce distinct current signals.

18. The method of claim 17, further comprising analyzing the change in detected current between the cis and trans chambers for the distinct current signals.

19. The method of claim 11, wherein using the change in detected current to sense an individual molecule of the reactive analyte comprises determining the identity and concentration of at least one reactive analyte.

20. The method of claim 11, wherein the reactive analyte irreversibly covalently bonds to the protein pore, further comprising introducing a chemical capable of reacting with the analyte to produce a second signal.

* * * * *